United States Patent [19]

Law

[11] 4,160,455
[45] Jul. 10, 1979

[54] HEATER FOR HEATING FLUID IN A BODY CAVITY

[75] Inventor: James T. Law, Edinburgh, Scotland

[73] Assignee: Ferranti Limited, Hollinwood, England

[21] Appl. No.: 815,282

[22] Filed: Jul. 13, 1977

[30] Foreign Application Priority Data

Jul. 14, 1976 [GB] United Kingdom ............... 29194/76

[51] Int. Cl.² ................................................ A61F 7/00
[52] U.S. Cl. ..................................... 128/400; 128/401
[58] Field of Search ......................... 128/400, 401, 231

[56] References Cited

U.S. PATENT DOCUMENTS

| | | | |
|---|---|---|---|
| 2,074,634 | 3/1937 | Ackermann | 128/401 |
| 2,076,638 | 4/1937 | Haynos | 128/401 |
| 2,190,384 | 2/1940 | Newman | 128/400 |
| 2,346,245 | 4/1944 | Zichlin | 128/401 |
| 2,734,508 | 2/1956 | Kozinski | 128/401 |
| 3,467,104 | 9/1969 | Burbridge et al. | 128/401 |
| 3,496,942 | 2/1970 | Shipley | 128/401 |
| 3,848,607 | 11/1974 | St. Clair | 128/401 |

*Primary Examiner*—John D. Yasko
*Attorney, Agent, or Firm*—Cameron, Kerkam, Sutton, Stowell & Stowell

[57] ABSTRACT

A heater for heating fluid within a body cavity of an animal say for heating tumours by irrigation, comprises a container having inlet and outlet ports through which fluid in the cavity is passed by an external pump, and a heating element in the container to heat at least some of the fluid that passes through the container. Pumping can be achieved by a fluid filled pipe coupled to the container, either directly by or by way of a diaphragm, and to a bellows or like arrangement for cyclicly varying the pressure of the fluid in the pipe and container.

17 Claims, 1 Drawing Figure

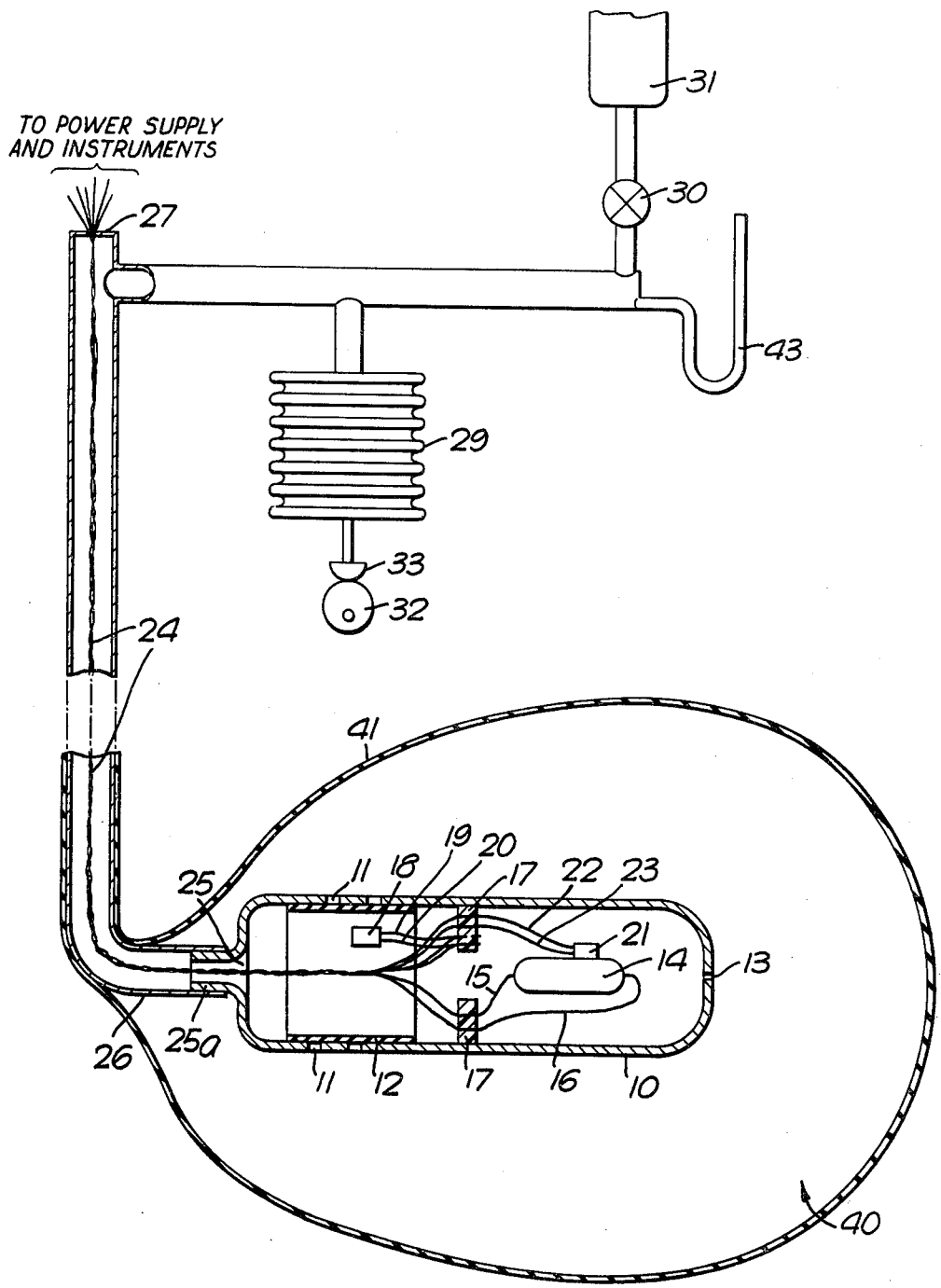

HEATER FOR HEATING FLUID IN A BODY CAVITY

This invention relates to heaters and in particular to heaters for heating body cavities of animals.

Malignant cells, such as in tumours, in animal tissue may, it is thought, be destroyed by increasing their temperature above the normal body temperature of the animal. The temperature at which the malignant cells die is lower than can be tolerated by most healthy cells but higher than that tolerated by some organs in the body such as the liver and the brain, so the whole body of the animal cannot be heated to the desired elevated temperature.

It is known to heat tumours by irrigating body cavities such as the stomach or bladder adjacent to the tumour with hot water ducted into and out of the cavity by pipes. A disadvantage of this technique is that the location of the ends of the pipes relative to each other is imprecise and it is difficult to ensure that circulation in the cavity is not confined to a small volume with the result that the temperature of the water in the cavity is non-uniform. Such non-uniform temperature is undesirable because the temperature to which the tumour is heated needs to be accurately controlled.

Another disadvantage is that the temperature of the water supplied for irrigation needs to be higher than the temperature required for the tumour and the pipes may burn or scald their passageway into the cavity.

It is an object of the present invention to provide a heater which, in use in heating body cavities of animals, mitigates one or more of the above problems.

According to the present invention a heater for heating fluid within a body cavity of an animal includes a container having inlet and outlet ports, pumping means for causing fluid to be drawn into the container through the inlet port and expelled through the outlet port, and a heating element located between the inlet and outlet ports so that at least some of the fluid passing through the container will be heated by the element.

The inlet port may include a one-way valve, the outlet port having no valve but being of much smaller cross-sectional area than the inlet port. When fluid is drawn into the container by way of the inlet port, an insignificant amount may also return through the outlet port.

Alternatively, each port may have a valve which opens when the other one closes.

Preferably, but not necessarily, the valves are operable by differences in pressure between the inside and the outside of the container, means for controlling the pressure difference comprising pressure varying means fluid-coupled to the container. Fluid in the coupling may be prevented from mixing with the heated fluid by a diaphragm.

Where the body cavity absorbs or secretes fluids the container may be sealed into a fluid-tight sac to contain the fluid to be heated. The sac may be of a flexible membrane which will deform when filled with fluid and conform to the interior of the body cavity.

Fluid temperature may be detected by a temperature sensing element located inside the container. A further temperature sensing element may be located in close proximity to the heating element.

An embodiment of the invention will be described by way of example and with reference to the accompanying drawing.

In the drawing a heater for heating fluid in a body cavity of an animal includes a cylindrical container 10. Inlet ports are provided by radial holes 11 towards one end of the container. A cylindrical elastic sleeve 12 inside the container, presses against and closes the holes 11.

An outlet port is provided by a small hole 13 at the other end of the cylindrical container. In the middle of the container is a heating element which consists of a vitreous resistor 14 supported by its leads 15 and 16 from an annular terminal block 17.

A temperature sensing element, in the form of a thermistor 18, is located in the container close to the inlet port. The thermistor is supported on leads 19 and 20 from the terminal block 17. A second temperature sensing element, in the form of a thermistor 21, is fastened to heating element 14 and connected by leads 22 and 23 to the terminal block. A group of corresponding wires 24 from the terminal passes through a hole 25 in the end of the container adjacent to the inlet port, and into a pipe 26. The pipe is connected to a flange 25A around hole 25. The cable exits from the pipe by way of a fluid-tight joint 27 and connects to power supplies and instruments (not shown).

The pipe 26 connects to a stainless steel bellows 29 and, by way of a stop-cock 30, to a fluid reservoir 31. The bellows 29 is actuated by means of a cam 32 acting against a follower 33 which is coupled to the end of the bellows.

In use, the container 10 is inserted into a body cavity 40, for example the bladder, which is to be heated. The bladder, container 10, pipe 26 and bellows are filled with water, then stop-cock 30 is closed to seal the system. Heating element 14 is connected to a power supply (not shown) and the thermistors to temperature indicators (not shown). Rotation of cam 32 operates the bellows and cyclically increases and decreases the pressure in the pipe 26, this pressure variation being coupled to the inside of the container 10 by the fluid in the pipe. When the pressure inside the container is less than that inside the cavity, water is drawn into the container through holes 11. The sleeve partially collapses to allow entry of the water. A small amount of water will be drawn in through outlet port 13 but can be ignored because the area of this hole is much smaller than that of the inlet port. When the pressure inside the container is higher than the pressure in the cavity, the sleeve seals holes 11 and water is expelled from the container by way of outlet port 13. Before passing through the outleter port, the fluid passes around, and is heated by, the vitreous resistor 14. Because the outlet hole 13 is small the water issues from it as a fairly high-speed jet and produces vigorous agitation of the fluid in the body cavity.

This agitation ensures that the water in the cavity, and the interior surface of the cavity are heated uniformly. The temperature of the fluid drawn in through the inlet port is sensed by thermistor 18 and the supply to the resistor 14 adjusted accordingly to achieve a desired temperature.

This adjustment is carried out automatically using a feedback system of conventional design (not shown). The second thermistor 21 senses the temperature of the heating element and serves to provide speedy indication of malfunction. For example, if an air bubble should form around part or all of the heating element, its temperature will increase quickly, be detected by the thermistor 21 and prompt remedial action can be detected.

In an alternative embodiment, the container is sealed into a rubber sac 41 to prevent contact between the fluid in the cavity and the interior surface of the cavity.

This alternative embodiment is advantageously used where the body cavity readily absorbs or secretes fluids, for example, the stomach. Also, because the sac isolates the fluid from the cavity surface, the fluid need not be sterile and non-toxic. For instance, water with a marker dye added might be used assisting other diagnosis and treatment.

The above-described embodiment uses the same fluid for coupling the bellows to the container as is used for heating the cavity. In operation some heated fluid will diffuse into the pipe 26. Where this is undesirable, for example, where the rubber sac is being used with a marker dye, e.g. a radio opaque dye, added to the heating fluid, diffusion can be prevented by means of a flexible diaphragm across the hole 25 in the end of the container. Such a diaphragm allows the use of other fluids for the fluid coupling, for example, air.

An advantage of the closed hydraulic system, even without the rubber sac and diaphragm, is that the pressure in the body cavity can be readily monitored by means of a manometer 43 shown connected into the pipe 26.

The valve arrangement of particular embodiment could be modified to operate in the reverse direction by fitting the sleeve 12 around the outside of the container. The holes 11 would then serve as outlet ports and the hole 13 as an inlet port. Where hole 13 is provided with a valve the direction in which it operates would have to be correspondingly reversed.

What I claim is:

1. A heater for heating fluid within a body cavity of an animal including a container adapted to be inserted into the body cavity and having inlet and outlet ports, pumping means for causing fluid to be drawn from the cavity into the container through the inlet port and expelled into the cavity through the outlet port, and a heating element located within the container between the inlet and outlet ports so that at least some of the fluid passing through the container will be heated by said element.

2. A heater as claimed in claim 1 in which the inlet port includes a one-way valve and the outlet port has a cross-sectional area small with respect to the inlet port whereby an insignificant amount of fluid is drawn in through the outlet port.

3. A heater as claimed in claim 2 in which the one-way valve is operable in response to a pressure difference between the inside and outside of the container caused by the pumping means.

4. A heater as claimed in claim 3 in which the valve comprises a layer of resilient material biased against the inlet port normally to close it and arranged to be moved to open the port by a pressure difference of the correct sense between the inside and outside of the container.

5. A heater as claimed in claim 1 in which the inlet and outlet ports each have associated therewith a one-way valve arranged such that one valve opens when the other closes.

6. A heater as claimed in claim 1 in which the pumping means comprises a fluid filled pipe coupled to the container and a pump operable to alternately increase and decrease the pressure of the fluid in the pipe.

7. A heater as claimed in claim 6 in which the pump comprises a bellows containing the coupling fluid and having a cam follower arranged to engage a rotatable cam.

8. A heater as claimed in claim 7 in which the bellows are formed of stainless steel.

9. A heater as claimed in claim 6 in which the fluid in the pipe is separated from the fluid in the container by a diaphragm.

10. A heater as claimed in claim 1 in which the container is sealed into a fluid-tight sac to contain the fluid to be heated.

11. A heater as claimed in claim 10 in which the sac is formed of a flexible membrane arranged to deform when filled with fluid to conform to the interior of the body cavity.

12. A heater as claimed in claim 1 in which the heating element comprises a vitreous resistor.

13. A heater as claimed in claim 1 including a temperature sensing element located in the container operable to provide a signal related to the temperature of the fluid passing through the container.

14. A heater as claimed in claim 13 in which the temperature sensing element is a thermistor.

15. A heater as claimed in claim 13 including a further temperature sensing element located in the container in close proximity with the heating element operable to provide a signal related to the temperature of the heating element.

16. A heater as claimed in claim 15 in which the further temperature sensing element is a thermistor.

17. A heater as claimed in claim 13 including control means responsive to the signal to the temperature sensing element to control the temperature of the heating element.

* * * * *